US011464402B2

(12) United States Patent
Ushiroda

(10) Patent No.: US 11,464,402 B2
(45) Date of Patent: Oct. 11, 2022

(54) MEDICAL DIMMING CONTROL APPARATUS AND DIMMING CONTROL METHOD

(71) Applicant: Sony Olympus Medical Solutions Inc., Tokyo (JP)

(72) Inventor: Hiroshi Ushiroda, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 126 days.

(21) Appl. No.: 16/259,089

(22) Filed: Jan. 28, 2019

(65) Prior Publication Data

US 2019/0274530 A1    Sep. 12, 2019

(30) Foreign Application Priority Data

Mar. 12, 2018   (JP) .............................. JP2018-043854

(51) Int. Cl.
*A61B 1/06* (2006.01)
*A61B 1/04* (2006.01)
(Continued)

(52) U.S. Cl.
CPC ........ *A61B 1/0646* (2013.01); *A61B 1/00186* (2013.01); *A61B 1/042* (2013.01);
(Continued)

(58) Field of Classification Search
CPC .............. A61B 1/00149; A61B 1/0016; A61B 1/00186; A61B 1/042; A61B 1/043; A61B 1/045; A61B 1/0638; A61B 1/0646; A61B 1/0661; A61B 1/06–0692; G02B 21/0012; G02B 21/22; G02B 23/24
(Continued)

(56) References Cited

U.S. PATENT DOCUMENTS

2004/0189822 A1* 9/2004 Shimada .............. H04N 5/2354
348/229.1
2007/0010714 A1* 1/2007 Negishi ................ A61B 1/0669
600/180

(Continued)

FOREIGN PATENT DOCUMENTS

CN    103860129 B    1/2015
JP    H05164976 A    6/1993
(Continued)

*Primary Examiner* — Brian T Pendleton
*Assistant Examiner* — Frank Johnson
(74) *Attorney, Agent, or Firm* — Xsensus LLP

(57) ABSTRACT

There is provided a medical dimming control apparatus including: a dimming control section configured to control a dimming in relation to an imaging of an observation target by an imaging device in accordance with a set dimming mode. The dimming mode at least includes a first dimming mode that controls the dimming at a first tracking speed and a second dimming mode that controls the dimming at a second tracking speed that is slower than the first tracking speed, and the dimming control section sets the first dimming mode on the basis of a change in an imaging-related behavior in the imaging device, and sets the second dimming mode in a case of determining that a predetermined condition is satisfied while executing the control in accordance with the first dimming mode.

12 Claims, 6 Drawing Sheets

(51) Int. Cl.
*A61B 1/045* (2006.01)
*A61B 1/00* (2006.01)
*G02B 21/00* (2006.01)
*G02B 21/22* (2006.01)
*G02B 23/24* (2006.01)

(52) U.S. Cl.
CPC .......... *A61B 1/045* (2013.01); *G02B 21/0012* (2013.01); *G02B 21/22* (2013.01); *A61B 1/043* (2013.01); *A61B 1/0638* (2013.01); *A61B 1/0661* (2013.01); *G02B 23/24* (2013.01)

(58) Field of Classification Search
USPC ........................................................ 600/109
See application file for complete search history.

(56) References Cited

U.S. PATENT DOCUMENTS

| | | | | |
|---|---|---|---|---|
| 2008/0071140 | A1* | 3/2008 | Gattani | A61B 1/0005 600/117 |
| 2009/0091614 | A1* | 4/2009 | Gono | G01J 3/501 348/68 |
| 2009/0149713 | A1* | 6/2009 | Niida | G02B 23/2484 600/167 |
| 2013/0063618 | A1* | 3/2013 | Miyazaki | H04N 5/2354 348/221.1 |
| 2014/0081083 | A1* | 3/2014 | Morita | A61B 1/0646 600/109 |
| 2015/0305118 | A1* | 10/2015 | Beghelli | H05B 47/11 315/158 |
| 2016/0120396 | A1* | 5/2016 | Homan | A61B 1/05 600/109 |
| 2017/0095297 | A1* | 4/2017 | Richmond | A61B 1/00193 |
| 2018/0160051 | A1* | 6/2018 | Schaefer | H04N 5/265 |

FOREIGN PATENT DOCUMENTS

| | | | |
|---|---|---|---|
| JP | 2000152913 A | 6/2000 | |
| JP | 2007097711 A | 4/2007 | |
| JP | 2009-273577 | 11/2009 | |
| JP | 2009273577 | * 11/2009 | ............. A61B 19/00 |
| JP | 2012085790 A | 5/2012 | |
| JP | 2017038285 A | 2/2017 | |
| WO | WO-2017057133 A1 | 4/2017 | |

* cited by examiner

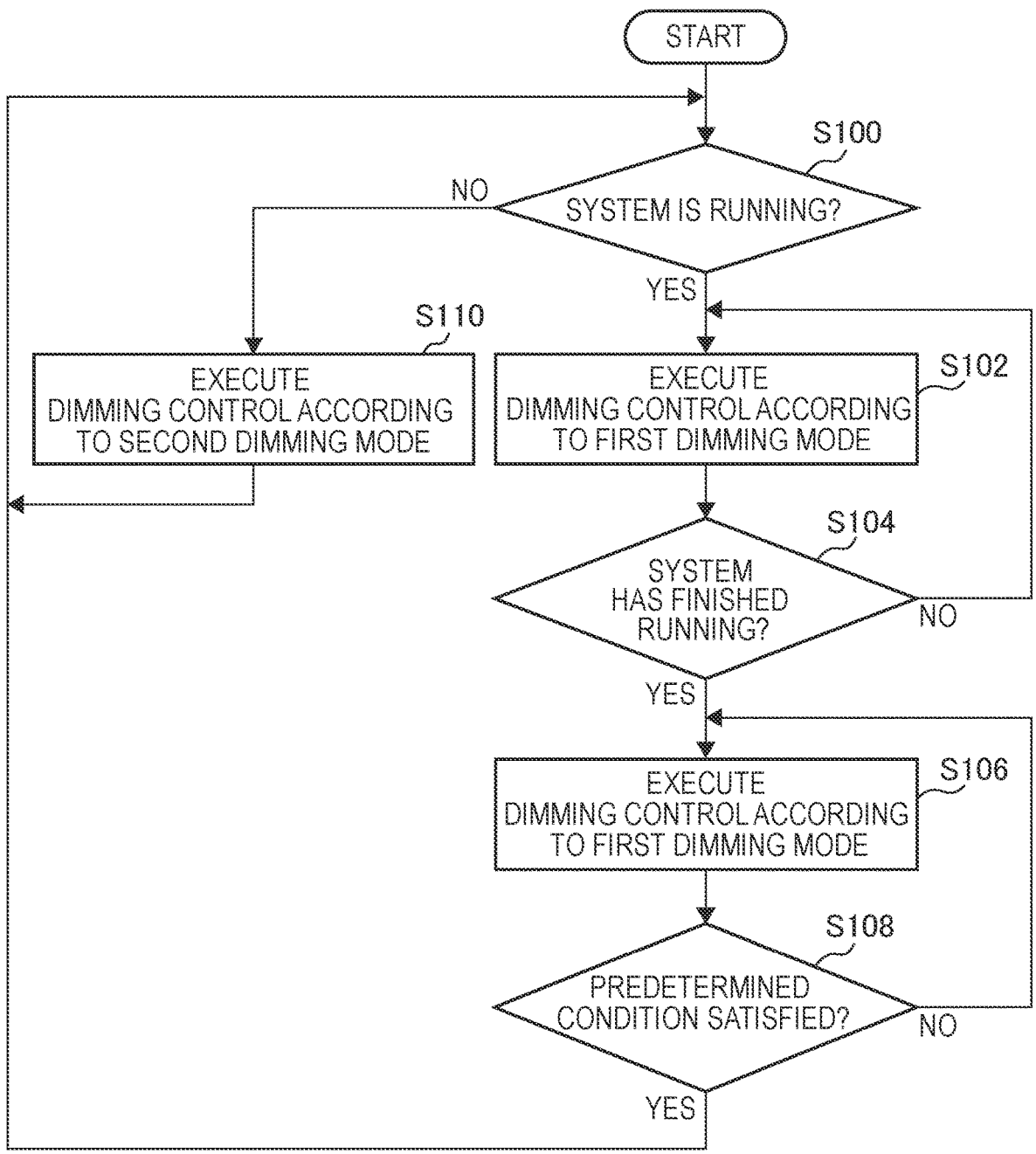

MEDICAL DIMMING CONTROL APPARATUS AND DIMMING CONTROL METHOD

CROSS REFERENCE TO RELATED APPLICATIONS

This application claims the benefit of Japanese Priority Patent Application JP 2018-043854 filed Mar. 12, 2018, the entire contents of which are incorporated herein by reference.

BACKGROUND

The present disclosure relates to a medical dimming control apparatus and a dimming control method.

Recently, in the medical field, to support microsurgery such as neurosurgical procedures, or to perform an endoscopic surgery, for example, medical observation apparatus capable of enlarged observation of an observation target such as an affected area are used in some cases. Examples of medical observation apparatus include a medical observation apparatus provided with an optical microscope, and a medical observation apparatus provided with an imaging device that functions as an electronic imaging microscope. In the following, the above medical observation apparatus provided with an optical microscope will be designated an "optical medical observation apparatus". Also, in the following, the above medical observation apparatus provided with an imaging device will be designated an "electronic imaging medical observation apparatus" or simply a "medical observation apparatus" in some cases. Also, in the following, a captured image (a moving image or a still image; the same applies hereinafter) in which an observation target is captured by an imaging device provided in a medical observation apparatus is denoted a "medical captured image".

With an electronic imaging medical observation apparatus, along with the increased image quality of imaging devices, the increased image quality of display apparatus on which captured images are displayed, and the like, the same or higher image quality than an optical medical observation apparatus has come to be obtained. Also, because a user who uses an electronic imaging medical observation apparatus (for example, medical personnel such as a surgeon or a surgeon's assistant; the same applies hereinafter) is not required to peer into an eyepiece lens included in an optical microscope like in the case of using an optical medical observation apparatus, it is possible to move the position of the imaging device more freely. For this reason, using an electronic imaging medical observation apparatus has an advantage of enabling more flexible support of microsurgery, and in the medical field, utilization of electronic imaging medical observation apparatus is progressing.

Among these, technologies that keep the image of an affected area or a surgical site on an observation screen at an optimal brightness, even if various treatment tools enter and exit the operative field during surgery, are being developed. Examples of the above technologies include the technology described in JP 2009-273577A.

SUMMARY

For example, with the technology described in JP 2009-273577A, controls with different dimming control may be switched to correspond with a result of detecting a varying/stopped state of the observation field. In the case in which the technology described in JP 2009-273577A is used, dimming is executed rapidly when the observation field is in an unstable state, but dimming slows the instant the observation field becomes a fixed state. For this reason, in the case in which the technology described in JP 2009-273577A is used, when dimming according to the dimming control executed while the observation field is in an unstable state has not completed by the time the observation field becomes a fixed state, it takes time for the dimming to reach a completed state.

The present disclosure proposes a novel and improved medical dimming control apparatus and dimming control method capable of executing dimming control better suited to the imaging of an observation target by an imaging device.

According to an embodiment of the present disclosure, there is provided a medical dimming control apparatus including: a dimming control section configured to control a dimming in relation to an imaging of an observation target by an imaging device in accordance with a set dimming mode. The dimming mode at least includes a first dimming mode that controls the dimming at a first tracking speed and a second dimming mode that controls the dimming at a second tracking speed that is slower than the first tracking speed, and the dimming control section sets the first dimming mode on the basis of a change in an imaging-related behavior in the imaging device, and sets the second dimming mode in a case of determining that a predetermined condition is satisfied while executing the control in accordance with the first dimming mode.

In addition, according to an embodiment of the present disclosure, there is provided a dimming control method executed by a medical dimming control apparatus, the dimming control method including: controlling a dimming in relation to an imaging of an observation target by an imaging device in accordance with a set dimming mode. The dimming mode at least includes a first dimming mode that controls the dimming at a first tracking speed and a second dimming mode that controls the dimming at a second tracking speed that is slower than the first tracking speed, and the controlling sets the first dimming mode on the basis of a change in an imaging-related behavior in the imaging device, and sets the second dimming mode in a case in which a predetermined condition is determined to be satisfied while executing the control in accordance with the first dimming mode.

According to an embodiment of the present disclosure, it is possible to execute dimming control better suited to the imaging of an observation target by an imaging device.

Note that the effects described above are not necessarily limitative. With or in the place of the above effects, there may be achieved any one of the effects described in this specification or other effects that may be grasped from this specification.

BRIEF DESCRIPTION OF THE DRAWINGS

FIG. 6 is a flowchart illustrating one example of processes related to the dimming control method according to the present embodiment.

DETAILED DESCRIPTION OF THE EMBODIMENT(S)

Figure 1:
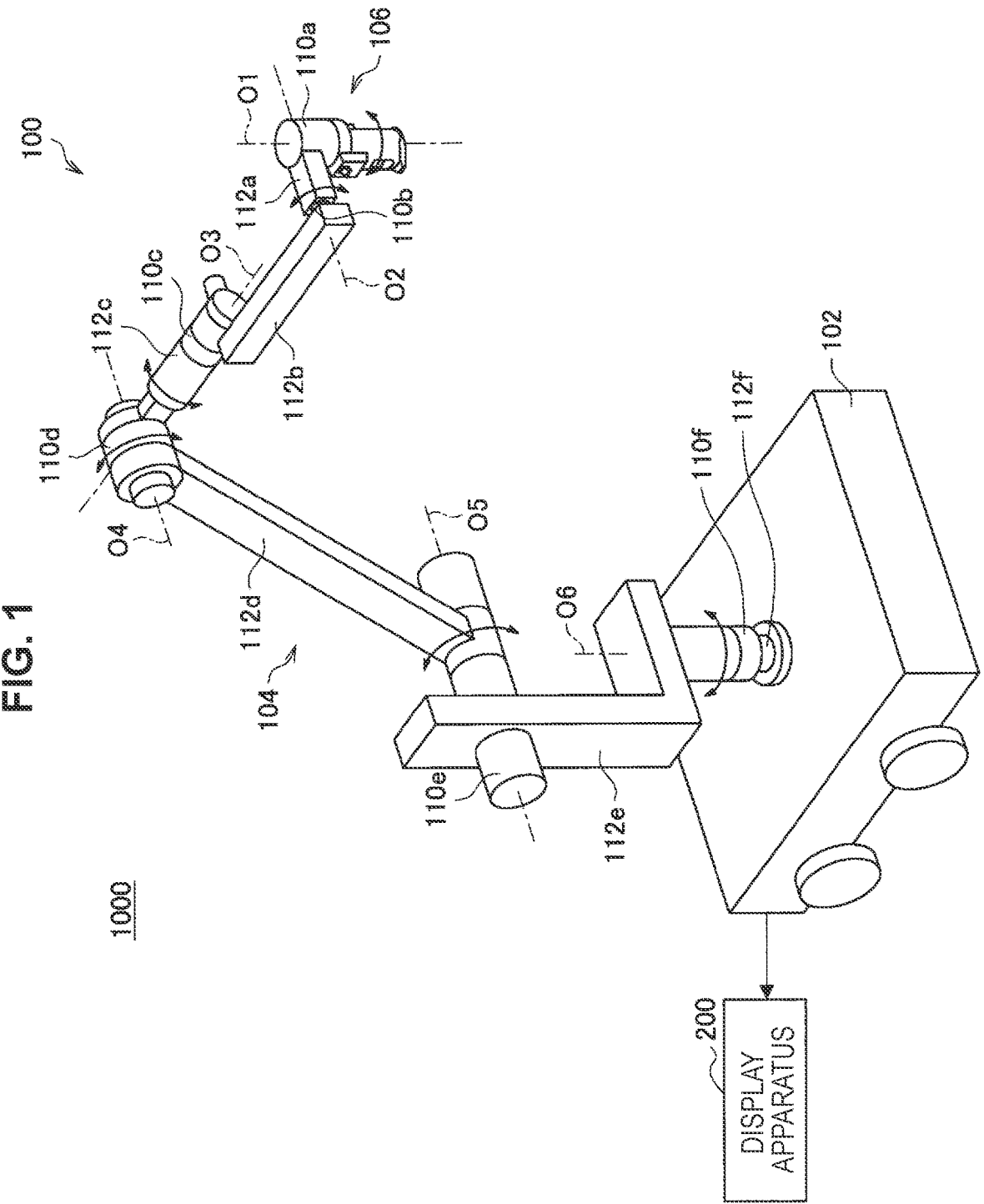
FIG. 1 is an explanatory diagram illustrating a first example of a configuration of a medical observation system according to the present embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description hereinafter will proceed in the following order.

1. Medical observation system according to present embodiment and dimming control method according to present embodiment
　[1] Configuration of medical observation system
　　[1-1] Medical observation system according to first example
　　[1-2] Medical observation system according to second example
　　[1-3] Functional configuration of medical observation apparatus
　[2] Dimming control method according to present embodiment
　[3] Example of advantageous effects exhibited by use of dimming control method according to present embodiment
2. Program according to present embodiment (Medical Observation System According to Present Embodiment and Dimming Control Method According to Present Embodiment)

Hereinafter, an example of a medical observation system according to the present embodiment will be described, while a dimming control method according to the present embodiment will also be described.

Hereinafter, the case in which the medical observation apparatus according to the present embodiment executes processes related to the dimming control method according to the present embodiment, that is, the case in which the medical observation apparatus according to the present embodiment functions as a medical dimming control apparatus will be described primarily. Note that in the medical observation system according to the present embodiment, the apparatus that functions as the medical dimming control apparatus is not limited to the medical observation apparatus according to the present embodiment. For example, in the medical observation system according to the present embodiment, the display apparatus described later may also function as the medical dimming control apparatus that executes the processes related to the dimming control method according to the present embodiment. For example, in the medical observation system according to the present embodiment, any apparatus capable of executing the processes related to the dimming control method according to the present embodiment, such as a medical controller, may function as the medical dimming control apparatus.

[1] Configuration of Medical Observation System

[1-1] Medical Observation System According to First Example

FIG. 1 is an explanatory diagram illustrating a first example of the configuration of a medical observation system 1000 according to the present embodiment. The medical observation system 1000 illustrated in FIG. 1 includes a medical observation apparatus 100 and a display apparatus 200, for example.

Note that the medical observation system according to the first example is not limited to the example illustrated in FIG. 1.

For example, the medical observation system according to the first example additionally may include a medical control apparatus (not illustrated) that controls various operations in the medical observation apparatus 100. In the medical observation system 1000 illustrated in FIG. 1, as described later, an example is illustrated in which, by providing the medical observation apparatus 100 with a control section (described later), the medical observation apparatus 100 includes the functions of the medical control apparatus (not illustrated).

Examples of the medical control apparatus (not illustrated) include, a "medical controller", a "computer such as a server", and the like. Also, the medical control apparatus (not illustrated) may be, for example, an integrated circuit (IC) that can be embedded in equipment like the above.

Additionally, the medical observation system according to the first example may also be a configuration that includes one or both of the medical observation apparatus 100 and the display apparatus 200. In the case of including multiple medical observation apparatuses 100, in each medical observation apparatus 100, processes according to the dimming control method described later are performed. Also, in the case in which the medical observation system according to the first example is a configuration that includes multiple medical observation apparatuses 100 and display apparatuses 200, the medical observation apparatus 100 and the display apparatus 200 may be associated in a 1-to-1 manner, or multiple medical observation apparatuses 100 may be associated with a single display apparatus 200. In the case in which multiple medical observation apparatuses 100 are associated with a single display apparatus 200, which medical observation apparatus 100 provides a medical captured image to be displayed on a display screen is switched by performing a switching operation or the like in the display apparatus 200, for example.

Figure 2:
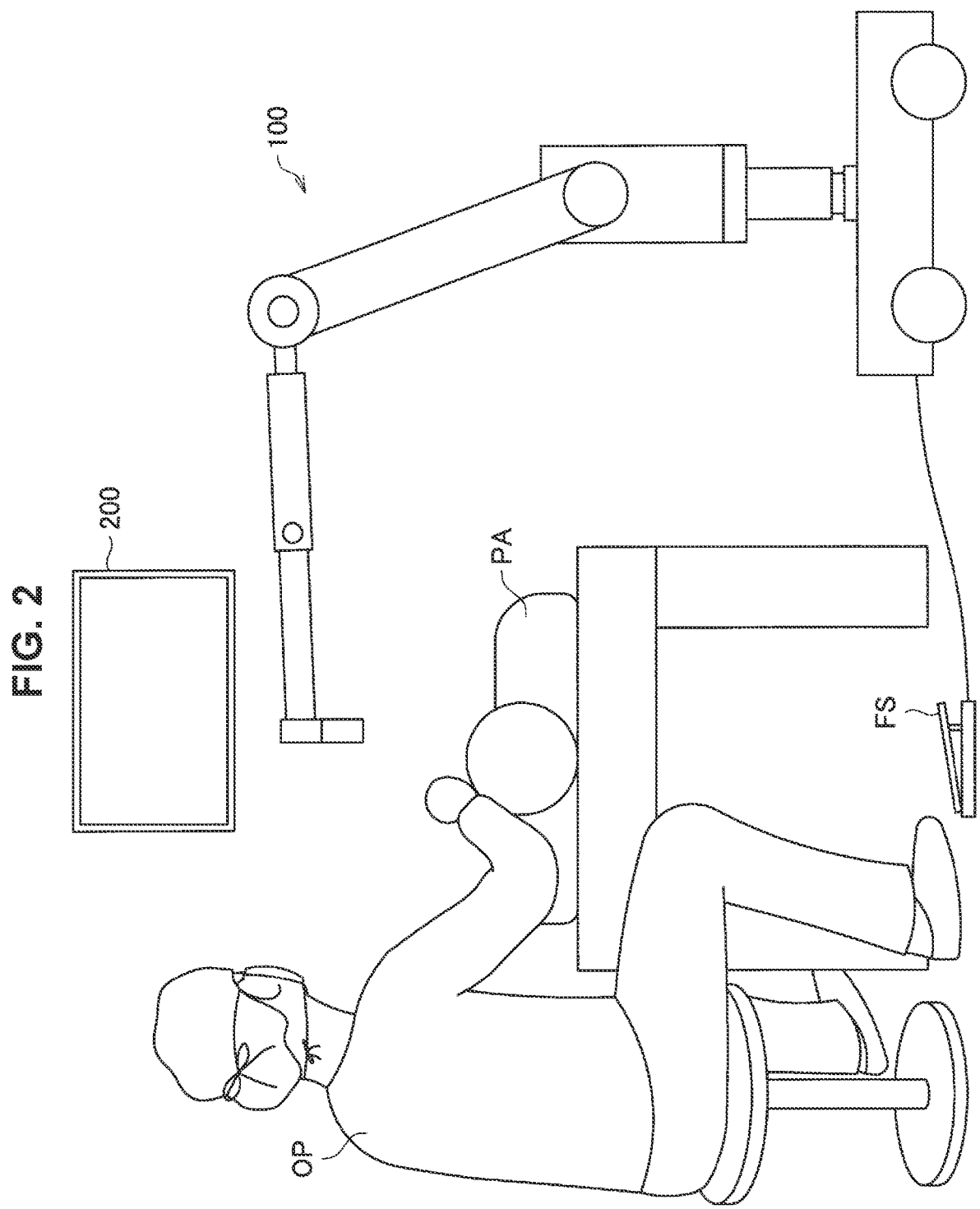
FIG. 2 is an explanatory diagram illustrating an example of a use case in which the medical observation system according to the present embodiment is used.

FIG. 2 is an explanatory diagram illustrating one example of a use case in which the medical observation system 1000 according to the present embodiment is used, and illustrates one example of a use case in which the medical observation system 1000 according to the first example is used.

By an imaging device (described later) provided in the medical observation apparatus 100, an observation target patient PA (a patient who undergoes a medical procedure) is imaged. A captured image that captures the above patient who undergoes a medical procedure, corresponds to an example of a "medical captured image".

The medical captured image captured in the medical observation apparatus 100 is displayed on a display screen of a display apparatus 200. Subsequently, a surgeon OP (an example of a user of the medical observation apparatus 100) who performs a medical procedure by using the medical observation apparatus 100 performs the medical procedure on the patient PA while looking at the medical captured image displayed on the display screen of the display apparatus 200.

Also, the surgeon OP operates an operating device external to the medical observation apparatus 100, such as a footswitch FS, or an operating device (described later) provided in the medical observation apparatus 100, thereby causing an arm (described later) and the imaging device (described later) provided in the medical observation apparatus 100 to operate, and putting the medical observation apparatus 100 into a desired state.

Hereinafter, each apparatus included in the medical observation system 1000 according to the first example illustrated in FIG. 1 will be described.

[1-1-1] Display Apparatus 200

The display apparatus 200 is a display device in the medical observation system 1000 according to the first example, and corresponds to an external display device from the perspective of the medical observation apparatus 100. The display apparatus 200 displays various images on a display screen, such as a medical captured image taken in the medical observation apparatus 100, or an image related to a user interface (UI), for example. Also, the display apparatus 200 may include a configuration capable of 3D display according to any method. The display on the display apparatus 200 is controlled by, for example, the medical observation apparatus 100 or the medical control apparatus (not illustrated).

In the medical observation system 1000, the display apparatus 200 is installed in an arbitrary location visible to a person involved in a surgery inside an operating room, such as on a wall, the ceiling, or the floor of the operating room.

Examples of the display apparatus 200 include a liquid crystal display, an organic electro-luminescence (EL) display, a cathode ray tube (CRT) display, and the like.

Note that the display apparatus 200 is not limited to the example illustrated above. For example, the display apparatus 200 may also be an arbitrary wearable apparatus that is used by being worn on the body of the surgeon or the like, such as a head-mounted display, an eyewear-type apparatus, or the like.

The display apparatus 200 runs on electric power supplied from an internal power source such as a battery provided in the display apparatus 200, on electric power supplied from a connected external power source, or the like, for example.

[1-1-2] Medical Observation Apparatus 100

The medical observation apparatus 100 illustrated in FIG. 1 is an electronic imaging medical observation apparatus. For example, in the case in which the medical observation apparatus 100 illustrated in FIG. 1 is used during surgery, the surgeon (one example of the user of the medical observation apparatus 100) observes an operating site (an affected area) while referring to a medical captured image which has been taken by the medical observation apparatus 100 and displayed on the display screen of the display apparatus 200, and performs various treatments, such as techniques depending on the surgical procedure, on the operating site.

As illustrated in FIG. 1, the medical observation apparatus 100 is provided with a base 102, an arm 104, and an imaging device 106, for example.

Additionally, although not illustrated in FIG. 1, the medical observation apparatus 100 may also be provided with, for example, one or multiple processors (not illustrated) including a computational circuit such as a microprocessing unit (MPU), read-only memory (ROM; not illustrated), random access memory (RAM; not illustrated), a recording medium (not illustrated), and a communication device (not illustrated). The medical observation apparatus 100 runs on electric power supplied from an internal power source such as a battery provided in the medical observation apparatus 100, on electric power supplied from a connected external power source, or the like, for example.

The one or multiple processors (not illustrated) function as the control section in the medical observation apparatus 100 (described later). The ROM (not illustrated) stores programs and control data such as computational parameters used by the one or multiple processors (not illustrated). The RAM (not illustrated) temporarily stores programs executed by the one or multiple processors (not illustrated), or the like.

The recording medium (not illustrated) functions as a storage section (not illustrated) in the medical observation apparatus 100. A variety of data is stored on the recording medium (not illustrated), including data related to the dimming control method according to the present embodiment, and various applications, for example. Herein, examples of the recording medium (not illustrated) include a magnetic recording medium such as a hard disk, non-volatile memory such as flash memory, and the like. Additionally, the recording medium (not illustrated) may also be removable from the medical observation apparatus 100.

The communication device (not illustrated) is a communication device provided in the medical observation apparatus 100, and fulfills a role of communicating in a wireless or wired manner with an external apparatus such as the display apparatus 200. Herein, examples of the communication device (not illustrated) include an IEEE 802.15.1 port and transmitting-receiving circuit (wireless communication), an IEEE 802.11 port and transmitting-receiving circuit (wireless communication), a communication antenna and a RF circuit (wireless communication), a LAN terminal and a transmitting-receiving circuit (wired communication), and the like.

[1-1-2-1] Base 102

The base 102 is the base of the medical observation apparatus 100. One end of the arm 104 is connected to the base 102, and the base 102 supports the arm 104 and the imaging device 106.

Also, casters are provided on the base 102, for example, and the medical observation apparatus 100 contacts the floor through the casters. By providing the casters, the medical observation apparatus 100 is able to move easily over the floor by the casters.

[1-1-2-2] Arm 104

The arm 104 includes multiple links joined to each other by joint sections.

In addition, the arm 104 supports the imaging device 106. The imaging device 106 supported by the arm 104 is movable three-dimensionally, and after moving, the position and the attitude of the imaging device 106 are maintained by the arm 104.

More specifically, the arm 104 includes, for example, multiple joint sections 110a, 110b, 110c, 110d, 110e, and 110f, and multiple links 112a, 112b, 112c, 112d, 112e, and 112f rotatably joined to each other by the joint sections 110a, 110b, 110c, 110d, 110e, and 110f. The rotatable range of each of the joint sections 110a, 110b, 110c, 110d, 110e, and 110f is set arbitrarily during the design stage, the manufacturing stage, or the like so that the desired motion of the arm 104 is realized.

In other words, in the medical observation apparatus 100 illustrated in FIG. 1, six degrees of freedom are realized in relation to the movement of the imaging device 106 by six rotation axes (first axis O1, second axis O2, third axis O3, fourth axis O4, fifth axis O5, and sixth axis O6) corresponding to the six joint sections 110a, 110b, 110c, 110d, 110e, and 110*f* included in the arm 104. More specifically, in the medical observation apparatus 100 illustrated in FIG. 1, motion with six degrees of freedom, including three degrees of translational freedom and three degrees of rotational freedom, is realized.

Actuators (not illustrated) are provided in each of the joint sections 110*a*, 110*b*, 110*c*, 110*d*, 110*e*, and 110*f*. Each of the joint sections 110*a*, 110*b*, 110*c*, 110*d*, 110*e*, and 110*f* rotates about the corresponding rotation axis by the driving of the actuators (not illustrated). The driving of the actuators (not illustrated) is controlled by, for example, a processor that functions as the control section described later, or an external medical control apparatus (not illustrated).

Each of the joint sections 110*a*, 110*b*, 110*c*, 110*d*, 110*e*, and 110*f* may be provided with angle sensors (not illustrated) capable of detecting a rotational angle for each of six rotation axes. The angle sensors may be, for example, rotary encoders, or any sensors capable of obtaining a rotational angle for each of six rotation axes, such as angular velocity sensors.

By having each of the joint sections 110*a*, 110*b*, 110*c*, 110*d*, 110*e*, 110*f* rotate about the corresponding rotation axis by the driving of the actuators (not illustrated), various operations of the arm 104, such as extending and contracting (folding up) the arm 104, for example, are realized.

The joint section 110*a* has an approximately cylindrical shape, and supports the imaging device 106 (the top end of the imaging device 106 in FIG. 1) on the front end portion of the joint section 110*a* (the bottom end portion in FIG. 1), so as to allow revolution about a rotation axis (first axis O1) parallel to the central axis of the imaging device 106. Herein, the medical observation apparatus 100 is configured so that the first axis O1 is aligned with the optical axis in the imaging device 106. In other words, by causing the imaging device 106 to revolve about the first axis O1 illustrated in FIG. 1, the medical captured image captured by the imaging device 106 becomes an image which has changed so that the field of view rotates.

The link 112*a* is an approximately rod-shaped member, and securely supports the joint section 110*a*. The link 112*a* extends in a direction orthogonal to the first axis O1, for example, and is connected to the joint section 110*b*.

The joint section 110*b* has an approximately cylindrical shape, and supports the link 112*a* so as to allow revolution about a rotation axis (second axis O2) orthogonal to the first axis O1. Also, the link 112*b* is securely connected to the joint section 110*b*.

The link 112*b* is an approximately rod-shaped member, and extends in a direction orthogonal to the second axis O2. Also, each of the joint section 110*b* and the joint section 110*c* is connected to the link 112*b*.

The joint section 110*c* has an approximately cylindrical shape, and supports the link 112*b* so as to allow revolution about a rotation axis (third axis O3) mutually orthogonal to each of the first axis O1 and the second axis O2. Also, one end of the link 112*c* is securely connected to the joint section 110*c*.

Herein, by having the front end side (the side on which the imaging device 106 is provided) of the arm 104 revolve about the second axis O2 and the third axis O3, the imaging device 106 can be made to move so that the position of the imaging device 106 in the horizontal plane is changed. In other words, in the medical observation apparatus 100, controlling the rotation about the second axis O2 and the third axis O3 makes it possible to move the field of view of the medical captured image in a flat plane.

The link 112*c* is a member in which one end has an approximately cylindrical shape, and the other end has an approximately rod-like shape. On the side of the one end of the link 112*c*, the joint section 110*c* is securely connected so that the central axis of the joint section 110*c* and the central axis of the approximately cylindrical shape are the same. Also, on the side of the other end of the link 112*c*, the joint section 110*d* is connected.

The joint section 110*d* has an approximately cylindrical shape, and supports the link 112*c* so as to allow revolution about a rotation axis (fourth axis O4) orthogonal to the third axis O3. The link 112*d* is securely connected to the joint section 110*d*.

The link 112*d* is an approximately rod-shaped member, and extends orthogonally to the fourth axis O4. One end of the link 112*d* is securely connected to the joint section 110*d* so as to abut the approximately cylindrical side face of the joint section 110*d*. Also, the joint section 110*e* is connected to the other end of the link 112*d* (the end on the opposite side of the side where the joint section 110*d* is connected).

The joint section 110*e* has an approximately cylindrical shape, and supports one end of the link 112*d* so as to allow revolution about a rotation axis (fifth axis O5) parallel to the fourth axis O4. Also, one end of the link 112*e* is securely connected to the joint section 110*e*.

Herein, the fourth axis O4 and the fifth axis O5 are rotation axis about which the imaging device 106 may be moved in the vertical direction. By having the front end side (the side on which the imaging device 106 is provided) of the arm 104 revolve about the fourth axis O4 and the fifth axis O5, the position of the imaging device 106 in the vertical direction changes. Thus, by having the front end side (the side on which the imaging device 106 is provided) of the arm 104 revolve about the fourth axis O4 and the fifth axis O5, changing the distance between the imaging device 106 and an observation target, such as an operating site of a patient, becomes possible.

The link 112*e* is a member that includes a combination of a first member having an approximate L-shape with one edge extending in the vertical direction while the other edge extends in the horizontal direction, and a rod-like second member that extends vertically downward from the part of the first member that extends in the horizontal direction. The joint section 110*e* is securely connected to the part of the first member of the link 112*e* that extends in the vertical direction. Also, the joint section 110*f* is connected to the second member of the link 112*e*.

The joint section 110*f* has an approximately cylindrical shape, and supports the link 112*e* so as to allow revolution about a rotation axis (sixth axis O6) parallel to the vertical direction. Also, the link 112*f* is securely connected to the joint section 110*f*.

The link 112*f* is an approximately rod-shaped member, and extends in the vertical direction. The joint section 110*f* is connected to one end of the link 112*f*. Also, the other end of the link 112*f* (the end on the opposite side of the side where the joint section 110*f* is connected) is securely connected to the base 102.

By having the arm 104 include the configuration indicated above, in the medical observation apparatus 100, six degrees of freedom are realized with respect to the movement of the imaging device 106.

Note that the configuration of the arm 104 is not limited to the example indicated above.

For example, each of the joint sections 110*a*, 110*b*, 110*c*, 110*d*, 110*e*, and 110*f* of the arm 104 may be provided with a brake that restrains rotation in each of the joint sections

110a, 110b, 110c, 110d, 110e, and 110f. The brake according to the present embodiment may be a brake of an arbitrary method, such as a mechanically driven brake or an electrically driven electromagnetic brake, for example.

The driving of the above brakes is controlled by, for example, a processor that functions as the control section described later, or an external medical control apparatus (not illustrated). By controlling the driving of the above brakes, in the medical observation apparatus 100, the operating mode of the arm 104 is set. Examples of operating modes of the arm 104 include a locked mode and a free mode.

Herein, the locked mode according to the present embodiment is, for example, an operating mode in which the position and the attitude of the imaging device 106 are locked by using brakes to restrain rotation about each rotation axis provided in the arm 104. By having the arm 104 enter the locked mode, the operating state of the medical observation apparatus 100 becomes a locked state in which the position and the attitude of the imaging device 106 are locked.

Also, the free mode according to the present embodiment is an operating mode in which the above brakes are released, thereby allowing each rotation axis provided in the arm 104 to rotate freely. For example, in the free mode, the position and the attitude of the imaging device 106 are adjustable by direct operations performed by the surgeon. Herein, a direct operation according to the present embodiment means, for example, an operation in which the surgeon grips the imaging device 106 with his or her hand, and directly moves the imaging device 106.

[1-1-2-3] Imaging Device 106

The imaging device 106 is supported by the arm 104, and images an observation target such as an operating site of a patient, for example. Imaging in the imaging device 106 is controlled by, for example, a processor that functions as the control section described later, or an external medical control apparatus (not illustrated).

The imaging device 106 has a configuration corresponding to an electronic imaging microscope, for example.

Figure 3:
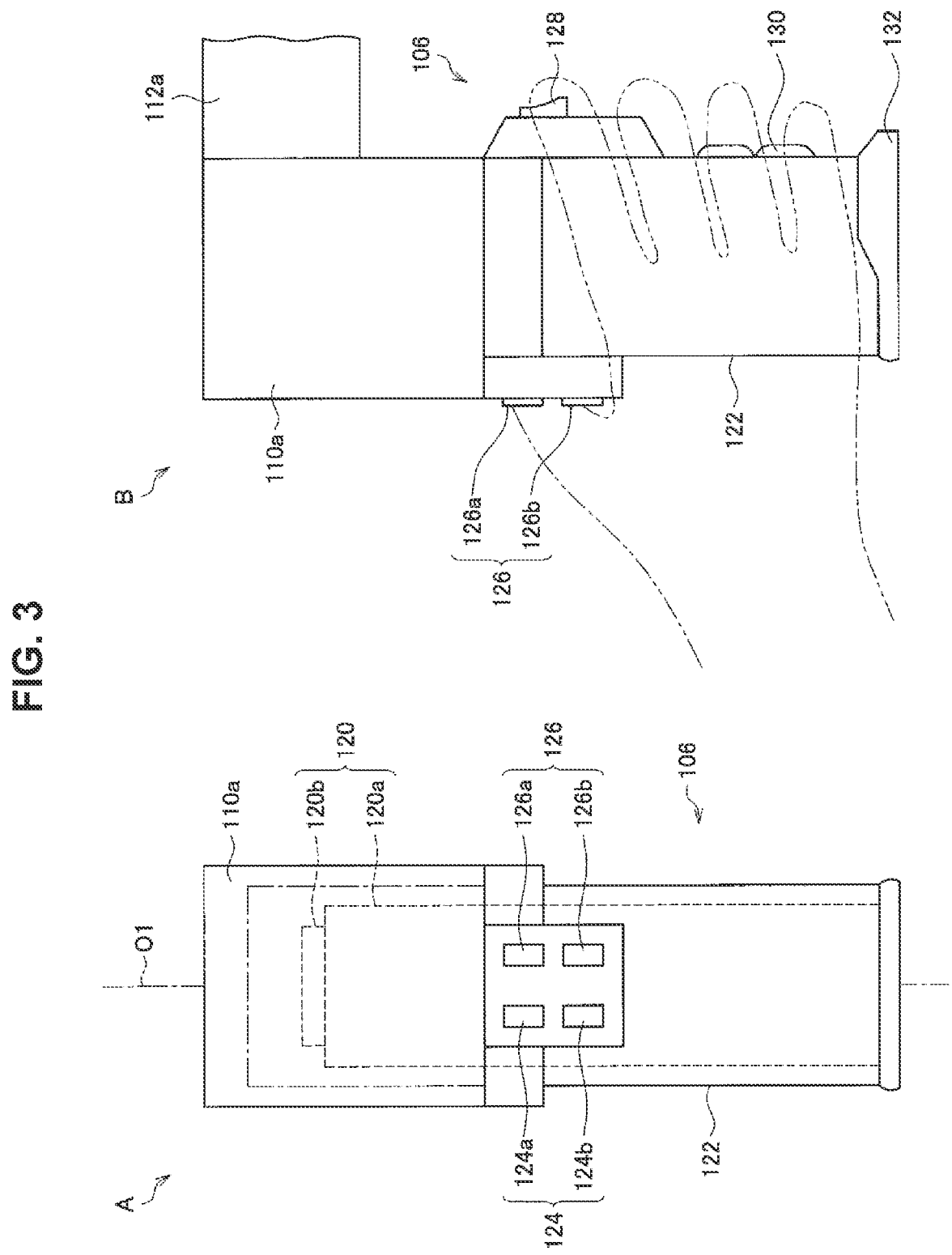
FIG. 3 is an explanatory diagram for explaining an example of the configuration of an imaging device provided in a medical observation apparatus according to the present embodiment.

FIG. 3 is an explanatory diagram for explaining an example of the configuration of the imaging device 106 provided in the medical observation apparatus 100 according to the present embodiment.

For example, the imaging device 106 includes an imaging member 120 and a barrel member 122 having an approximately cylindrical shape, with the imaging member 120 being provided inside the barrel member 122.

On an aperture on the bottom end of the barrel member 122 (the lower end in FIG. 3), for example, a cover glass (not illustrated) for protecting the imaging member 120 is provided.

Additionally, for example, a light source (not illustrated) is provided inside the barrel member 122, and during imaging, the subject is irradiated with illuminating light radiating from the light source through the cover glass. Reflected light (observation light) from the subject irradiated with illuminating light enters the imaging member 120 through the cover glass (not illustrated), whereby an image signal indicating the subject (an image signal indicating a medical captured image) is obtained by the imaging member 120.

As the imaging member 120, any of various known types of configurations used in an electronic imaging microscope section can be applied.

To give one example, the imaging member 120 includes an optical system 120a and an image sensor 120b including an imaging element that takes an image of an observation target with light transmitted through the optical system 120a, for example. The optical system 120a includes optical elements such as a mirror and one or multiple lenses, such as an objective lens, a zoom lens, and a focus lens, for example. Examples of the image sensor 120b include an image sensor using multiple imaging elements, such as a complementary metal-oxide semiconductor (CMOS) or a charge-coupled device (CCD).

The imaging member 120, by including two or more imaging devices provided with an optical system 120a and an image sensor 120b, for example, functions as what is called a stereo camera. In the configuration of the imaging device 106 that functions as a stereo camera, the optical system may be a Galileo optical system or a Greenough optical system.

Each imaging device included in the imaging member 120 is equipped with one or multiple functions typically provided in an electronic imaging microscope section, such as a zoom function (one or both of an optical zoom function and an electronic zoom function) and an autofocus (AF) function.

In addition, the imaging member 120 may also be configured to be capable of imaging at what are called high resolutions, such as 4K and 8K, for example. By configuring the imaging member 120 to be capable of imaging at high resolutions, it becomes possible to ensure a predetermined resolution (such as full HD image quality, for example), while also displaying an image on the display apparatus 200 having a large display screen, such as 50 inches or more, for example. For this reason, visibility is improved for the surgeon watching the display screen. Also, by configuring the imaging member 120 to be capable of imaging at high resolutions, even if the captured image is enlarged by the electronic zoom function and displayed on the display screen of the display apparatus 200, it is still possible to ensure a predetermined resolution. Furthermore, in the case of using the electronic zoom function to ensure a predetermined resolution, since it is possible to reduce the performance of the optical zoom function in the imaging device 106, the optical system of the imaging device 106 can be simplified, and the imaging device 106 can be configured more compactly.

In the imaging device 106, for example, various operating devices for controlling the operation of the imaging device 106 are provided. For example, in FIG. 3, a zoom switch 124, a focus switch 126, and an operating mode change switch 128 are provided on the imaging device 106. Note that the positions and shapes in which to provide the zoom switch 124, the focus switch 126, and the operating mode change switch 128 obviously are not limited to the example illustrated in FIG. 3.

The zoom switch 124 and the focus switch 126 are an example of an operating device for adjusting the imaging parameters in the imaging device 106.

The zoom switch 124 includes, for example, a zoom-in switch 124a that increases the zoom magnification (enlargement ratio), and a zoom-out switch 124b that decreases the zoom magnification. By performing an operation on the zoom switch 124, the zoom magnification is adjusted, and the zoom is adjusted.

The focus switch 126 includes, for example, a long-range focus switch 126a that increases the focal length to the observation target (subject), and a close-range focus switch 126b that decreases the focal length to the observation target. By performing an operation on the focus switch 126, the focal length is adjusted, and the focus is adjusted.

The operating mode change switch 128 is an example of an operating device for changing the operating mode of the arm 104 in the imaging device 106. By performing an operation on the operating mode change switch 128, the operating mode of the arm 104 is changed. Examples of operating modes of the arm 104 include a locked mode and a free mode, as described above.

One example of an operation with respect to the operating mode change switch 128 is an operation of pressing the operating mode change switch 128. For example, the operating mode of the arm 104 becomes the free mode while the surgeon is pressing the operating mode change switch 128, and the operating mode of the arm 104 becomes the locked mode when the surgeon is not pressing the operating mode change switch 128.

In addition, the imaging device 106 is provided with, for example, an anti-slip member 130 and a projecting member 132 in order to further raise operability, convenience, and the like when an operator who performs operations on various operation devices performs an operation.

The anti-slip member 130 is a member provided to prevent slipping of an operating body such as a hand when, for example, the operator performs an operation on the barrel member 122 with the operating body. The anti-slip member 130 is formed with a material having a large coefficient of friction, for example, and has a slip-resistant structure due to unevenness or the like.

The projecting member 132 is member provided to prevent an operating body such as a hand blocking the field of view of the optical system 120a when the operator performs an operation on the barrel member 122 with the operating body, or to prevent a cover glass (not illustrated) from becoming dirty due to the cover glass being contacted by the operating body when an operation is performed with the operating body.

Note that the position and shape in which each of the anti-slip member 130 and the projecting member 132 is provided obviously are not limited to the example illustrated in FIG. 3. In addition, the imaging device 106 does not have to be provided with one or both of the anti-slip member 130 and the projecting member 132.

The image signal (image data) generated by imaging in the imaging device 106 is subjected to image processing in a processor that functions as the control section described later, for example. Examples of image processing according to the present embodiment include one or multiple processes from among various processes such as gamma correction, white balance adjustment, image enlargement or reduction related to the electronic zoom function, and pixel interpolation, for example.

Also, the image processing according to the present embodiment may also include a process of estimating the brightness of the observation target on the basis of the image signal. For example, the process of estimating the brightness of the observation target on the basis of the image signal may be, for example, a process of generating a luminance image from the imaging signal and estimating the brightness of the observation target from the generated luminance image. The brightness of the observation target is estimated by computing the average of the luminance value for each pixel in the luminance image, for example. Note that an example of the process of estimating the brightness of the observation target on the basis of the image signal is not limited to the example illustrated above, and may be any process capable of estimating the brightness of the observation target on the basis of the image signal.

Note that in the case in which the medical observation system according to the present embodiment includes a medical control apparatus (not illustrated) that controls various operations in the medical observation apparatus 100, the image processing according to the present embodiment may also be performed in the medical control apparatus (not illustrated).

For example, the medical observation apparatus 100 transmits a display control signal and the image signal subjected to various image processing, such as gamma correction, to the display apparatus 200.

By transmitting the display control signal and the image signal to the display apparatus 200, on the display screen of the display apparatus 200, a medical captured image in which the observation target is imaged (for example, a captured image in which the operating site is imaged) is displayed enlarged or reduced at a desired magnification by one or both of the optical zoom function and the electronic zoom function.

The medical observation apparatus 100 illustrated in FIG. 1 includes the hardware configuration illustrated with reference to FIGS. 1 and 3, for example.

Note that the hardware configuration of the medical observation apparatus according to the present embodiment is not limited to the configuration illustrated with reference to FIGS. 1 and 3.

For example, the medical observation apparatus according to the present embodiment may also be a configuration not provided with the base 102, in which the arm 104 is directly attached to the ceiling, a wall, or the like of the operating room or the like. For example, in the case in which the arm 104 is attached to the ceiling, the medical observation apparatus according to the present embodiment becomes a configuration in which the arm 104 hangs down from the ceiling.

Also, although FIG. 1 illustrates an example in which the arm 104 is configured so that six degrees of freedom are realized with respect to the driving of the imaging device 106, the configuration of the arm 104 is not limited to a configuration whereby the degrees of freedom with respect to the driving of the imaging device 106 become six degrees of freedom. For example, it is sufficient to configure the arm 104 so that the imaging device 106 can move appropriately in accordance with the application, and factors such as the number and arrangement of joint sections and links, and the directions of the drive shafts of the joint sections can be set appropriately so that the arm 104 has the desired degrees of freedom.

Also, although FIGS. 1 and 3 illustrate an example in which various types of operating devices for controlling the operation of the imaging device 106 are provided on the imaging device 106, some or all of the operating devices illustrated in FIGS. 1 and 3 may also not be provided on the imaging device 106. To give one example, the various types of operating devices for controlling the operation of the imaging device 106 may also be provided in another part other than the imaging device 106 included in the medical observation apparatus according to the present embodiment. Also, to give another example, the various types of operating devices for controlling the operation of the imaging device 106 may also be external operating devices, such as a footswitch FS or a remote controller.

Additionally, the imaging device 106 may also have a configuration enabling switching among multiple observation modes. Observation modes according to the present embodiment may include, for example, an observation mode that executes imaging with natural light, an observation mode that executes imaging with special light, an observation mode that executes imaging by utilizing an image-enhancing observation technology such as narrow-band imaging (NBI), and the like. Special light according to the present embodiment refers to light in a specific wavelength band, such as light in the fluorescent wavelength band of fluorescent observation using 5-Aminolevulinic acid (5-ALA).

One example of the configuration of the imaging device 106 enabling switching among multiple observation modes is a "configuration provided with a filter that allows light of a specific wavelength band to pass through while not allowing light of other wavelength bands to pass through, and a movement mechanism that selectively disposes the filter on the optical path", for example. The specific wavelength band that the filter according to the present embodiment allows to pass through may be, for example, the wavelength band of near-infrared rays (for example, the wavelength band from approximately 0.7 [micrometers] to 2.5 [micrometers]), the fluorescent wavelength band for fluorescent observation using 5-ALA (for example, the wavelength band from approximately 0.6 [micrometers] to 0.65 [micrometers]), the fluorescent wavelength band of indocyanine green (ICG) (for example, the wavelength band from approximately 0.82 [micrometers] to 0.85 [micrometers]), or the like.

Note that the imaging device 106 may also be provided with multiple filters that allow different wavelength bands to pass through. Also, although the above illustrates an example in which imaging is executed with the light of a specific wavelength band by disposing a filter on the optical path, the configuration of the imaging device 106 for executing imaging with the light of a specific wavelength band obviously is not limited to the example illustrated above.

[1-2] Medical Observation System According to Second Example

The medical observation system 1000 according to the present embodiment is not limited to the configuration illustrated in the first example illustrated in FIG. 1. Next, as another example of the medical observation system 1000, one example of a configuration of the medical observation system 1000 including the medical observation apparatus 100 that functions as an endoscopic apparatus will be described.

Figure 4:
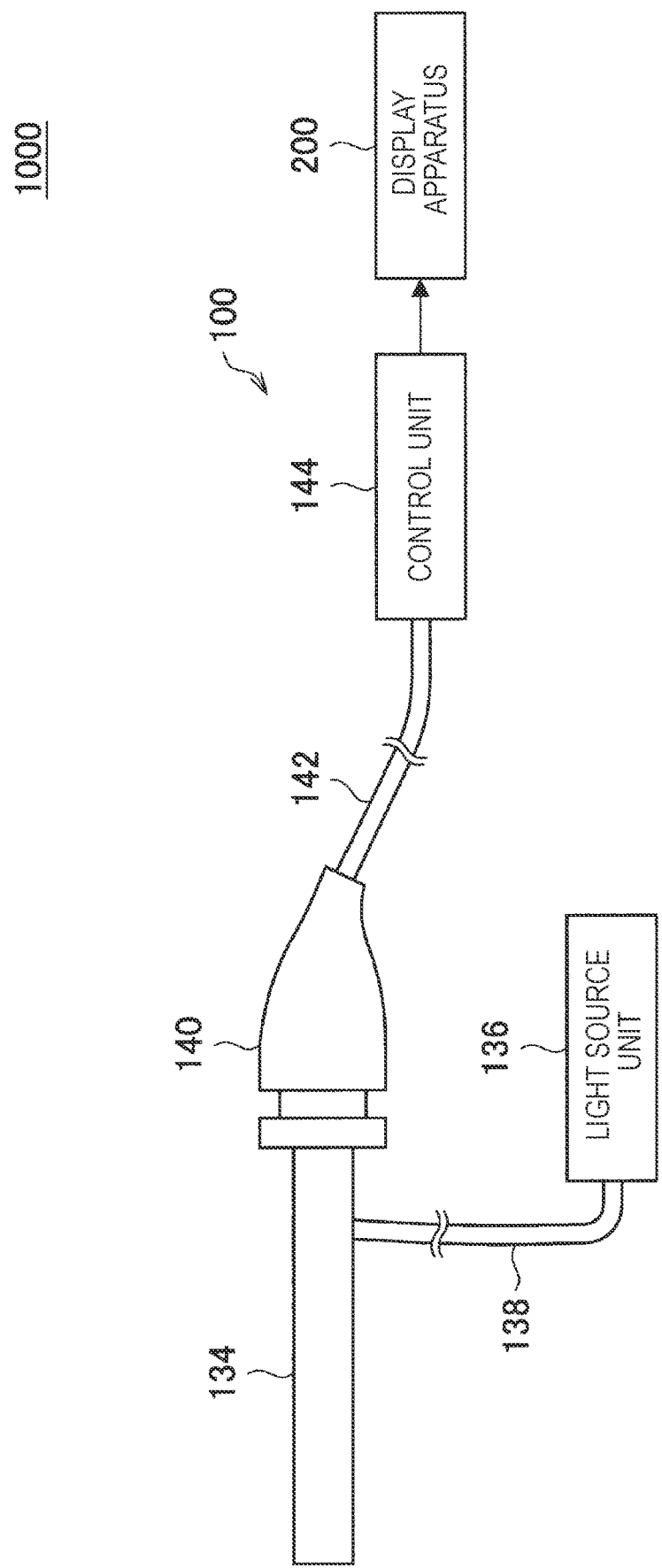
FIG. 4 is an explanatory diagram illustrating a second example of a configuration of a medical observation system according to the present embodiment.

FIG. 4 is an explanatory diagram illustrating a second example of the configuration of the medical observation system 1000 according to the present embodiment. The medical observation system 1000 illustrated in FIG. 4 includes the medical observation apparatus 100 and the display apparatus 200, for example. In the case in which the medical observation apparatus 100 illustrated in FIG. 4 is used during surgery, the surgeon observes the surgical site while referring to a medical captured image captured by the medical observation apparatus 100 and displayed on the display screen of the display apparatus 200, and performs various treatments, such as techniques depending on the surgical procedure, on the surgical site.

Note that the medical observation system according to the second example is not limited to the example illustrated in FIG. 4.

For example, in the medical observation system according to the second example, a holding apparatus (not illustrated) that holds the medical observation apparatus 100 may also be provided. The holding apparatus (not illustrated) may be an "arm in which the numbers of joint sections and links, their arrangement, the directions of the drive shafts of the joint sections, and the like are set up appropriately such that the arm has the desired degrees of freedom". In the medical observation system according to the second example provided with the holding apparatus (not illustrated), the medical observation apparatus 100 may also be detachable from the holding apparatus (not illustrated).

Also, for example, the medical observation system according to the second example additionally may include a medical control apparatus (not illustrated) that controls various operations in the medical observation apparatus 100, similarly to the medical observation system according to the first example.

Also, the medical observation system according to the second example may be a configuration including a plurality of one or both of the medical observation apparatus 100 and the display apparatus 200, similarly to the medical observation system according to the first example.

Hereinafter, each apparatus included in the medical observation system 1000 according to the second example illustrated in FIG. 4 will be described.

[1-2-1] Display Apparatus 200

The display apparatus 200 is a display device in the medical observation system 1000 according to the second example, and corresponds to an external display device from the perspective of the medical observation apparatus 100. The display apparatus 200 included in the medical observation system 1000 according to the second example is similar to the display apparatus 200 included in the medical observation system 1000 according to the first example.

[1-2-2] Medical Observation Apparatus 100

The medical observation apparatus 100 illustrated in FIG. 4 is provided with an insertion member 134, a light source unit 136, a light guide 138, a camera head 140, a cable 142, and a control unit 144, for example. The medical observation apparatus 100 runs on electric power supplied from an internal power source such as a battery provided in the medical observation apparatus 100, on electric power supplied from a connected external power source, or the like, for example.

The insertion member 134 has an elongated shape, and is internally provided with an optical system that condenses incident light. The front end of the insertion member 134 is inserted inside a body cavity of a patient. The rear end of the insertion member 134 is detachably connected to the front end of the camera head 140. Also, the insertion member 134 is connected to the light source unit 136 through the light guide 138, and is supplied with light from the light source unit 136.

The insertion member 134 may be formed with an inflexible material or a flexible material. Depending on the material used to form the insertion member 134, the medical observation apparatus 100 may be called a rigid scope or a flexible scope.

The light source unit 136 is connected to the insertion member 134 through the light guide 138. The light source unit 136 supplies light to the insertion member 134 through the light guide 138.

For example, the light source unit 136 includes multiple light sources that emit light of different wavelengths. The multiple light sources included in the light source unit 136 may be, for example, a light source that emits red light, a light source that emits green light, and a light source that emits blue light. The light source that emits red light may be one or multiple red light-emitting diodes, for example. The light source that emits green light may be one or multiple green light-emitting diodes, for example. The light source that emits blue light may be one or multiple blue light-emitting diodes, for example. Note that the multiple light sources included in the light source unit 136 obviously are not limited to the example illustrated above. For example, the light source unit 136 includes the multiple light sources on a single chip or includes the multiple light sources on multiple chips.

The light source unit 136 is connected to the control unit 144 in a wired or wireless manner, and the light emission in the light source unit 136 is controlled by the control unit 144.

Light supplied to the insertion member 134 is emitted from the front end of the insertion member 134, and irradiates an observation target such as tissue inside the body cavity of the patient. Additionally, reflected light from the observation target is condensed by the optical system inside the insertion member 134.

The camera head 140 has a function of imaging the observation target. The camera head 140 is connected to the control unit 144 through a signal transmission member, namely the cable 142.

The camera head 140 includes an image sensor, images the observation target by photoelectrically converting the reflected light from the observation target condensed by the insertion member 134, and outputs an image signal obtained by the imaging (a signal expressing the medical captured image) to the control unit 144 through the cable 142. The image sensor included in the camera head 140 may be, for example, an image sensor using multiple imaging elements such as CMOS and CCD elements.

In the medical observation apparatus 100 that functions as an endoscopic apparatus, for example, the insertion member 134, the light source unit 136, and the camera head 140 fulfill the role of an "imaging device that is inserted inside a body of a patient and images the inside of the body".

Note that the medical observation apparatus 100 that functions as an endoscopic apparatus may also be a configuration provided with multiple imaging devices that function as what is called a stereo camera, for example. In a configuration of imaging devices that function as a stereo camera, similarly to the medical observation apparatus 100 included in the medical observation system according to the first example, the optical system may be a Galileo optical system or a Greenough optical system.

The control unit 144 controls the imaging device. More specifically, the control unit 144 controls each of the light source unit 136 and the camera head 140.

Also, the control unit 144 includes a communication device (not illustrated), and transmits an image signal output from the camera head 140 to the display apparatus 200 by any form of wireless communication or any form of wired communication. The control unit 144 may also transmit an image signal and a display control signal to the display apparatus 200.

The communication device (not illustrated) included in the control unit 144 may be, for example, an IEEE 802.15.1 port and a transmitting-receiving circuit (wireless communication), an IEEE 802.11 port and a transmitting-receiving circuit (wireless communication), a communication antenna and an RF circuit (wireless communication), an optical communication device (wireless communication or wired communication), a LAN terminal and a transmitting-receiving circuit (wired communication), or the like. The communication device (not illustrated) may also be a configuration capable of communicating with one or multiple external apparatus by multiple communication methods.

In addition, the control unit 144 may execute predetermined processing on the image signal output from the camera head 140, and transmit the image signal that has been subjected to the predetermined processing to the display apparatus 200. The predetermined processing on the image signal may be, for example, white balance adjustment, image enlargement or reduction according to an electronic zoom function, pixel interpolation, and the like. Additionally, the predetermined processing on the image signal may also include the process of estimating the brightness of the observation target on the basis of the image signal described above.

Note that the control unit 144 may also store a medical captured image based on the image signal.

The control unit 144 may be a camera control unit (CCU), for example.

The medical observation apparatus 100 that functions as an endoscopic apparatus includes the hardware configuration illustrated with reference to FIG. 4, for example. In the medical observation apparatus 100 that functions as an endoscopic apparatus, for example, the insertion member 134, the light source unit 136, and the camera head 140 fulfill the role of the imaging device, and imaging in the imaging device is controlled by the control unit 144.

[1-3] Functional Configuration of Medical Observation Apparatus 100

Figure 5:
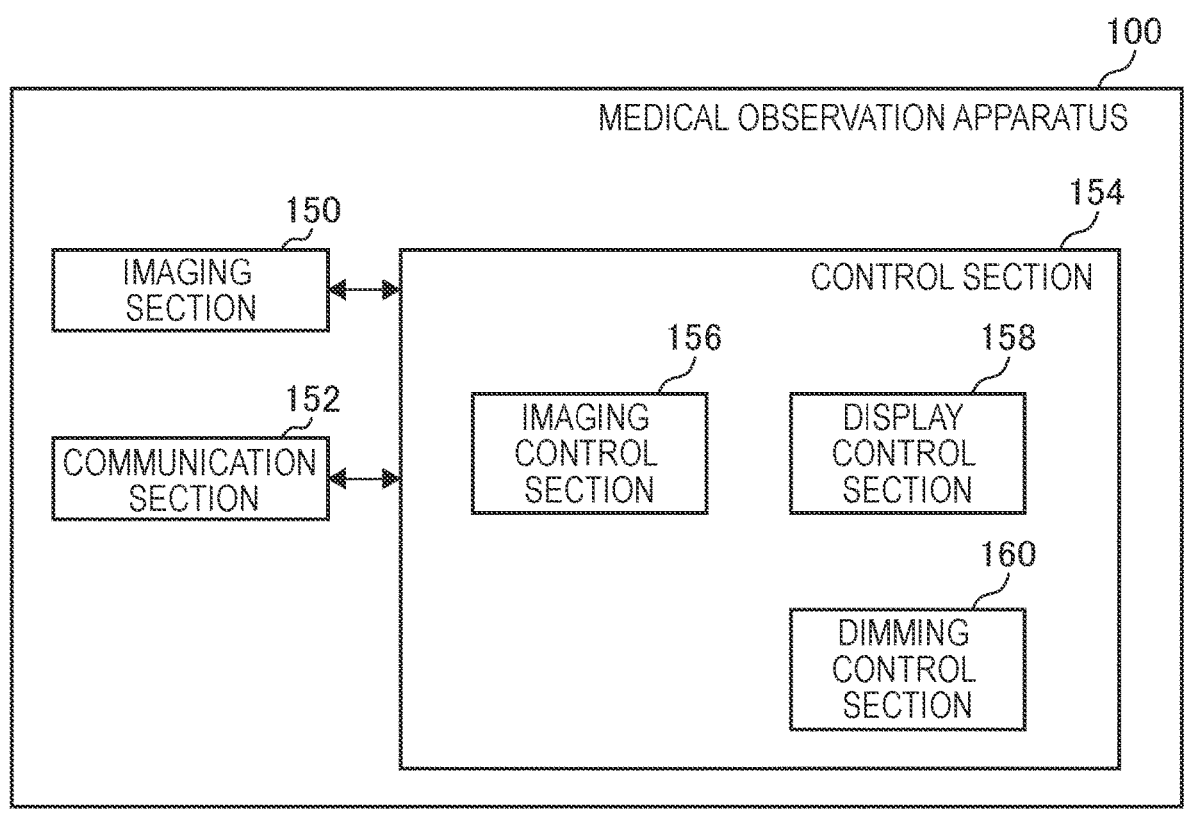
FIG. 5 is a function block diagram illustrating one example of a configuration of a medical observation apparatus according to the present embodiment.

Next, the medical observation apparatus 100 illustrated in FIGS. 1 and 4 will be described using function blocks. FIG. 5 is a function block diagram illustrating one example of the configuration of the medical observation apparatus 100 according to the present embodiment.

For example, the medical observation apparatus 100 is provided with an imaging section 150, a communication section 152, and a control section 154.

The imaging section 150 images the observation target. For example, the imaging section 150 includes the "imaging device 106" (in the case of the medical observation apparatus 100 illustrated in FIG. 1), or the "insertion member 134, the light source unit 136, and the camera head 140" (in the case of the medical observation apparatus 100 illustrated in FIG. 4). Imaging in the imaging section 150 is controlled by the control section 154, for example.

The communication section 152 is a communication device provided in the medical observation apparatus 100, and fulfills a role of communicating in a wireless or wired manner with an external apparatus such as the display apparatus 200. The communication section 152 includes the communication device (not illustrated) described above, for example. Communication in the communication section 152 is controlled by the control section 154, for example.

The control section 154 includes the processor (not illustrated) described above, for example, and fulfills a role of controlling the medical observation apparatus 100 overall. In addition, the control section 154 fulfills a role of leading the execution of the processes related to the dimming control method described later. Note that the processes related to the dimming control method in the control section 154 may also be executed in a distributed manner by multiple processing circuits (such as multiple processors, for example).

More specifically, the control section 154 includes an imaging control section 156, a display control section 158, and a dimming control section 160, for example.

The imaging control section 156 controls the imaging device included in the imaging section 150. Examples of the control of the imaging device include control of one or multiple functions typically provided in an electronic imaging microscope section, such as control of an AF function, including at least a zoom function (one or both of an optical zoom function and an electronic zoom function).

For example, the display control section 158 controls the display on the display apparatus 200 by conveying the display control signal and the image signal to the communication device (not illustrated) included in the communication section 152, and causing the display control signal and the image signal to be transmitted to the display apparatus 200. Note that the control of communication in the communication section 152 may also be performed by a communication control section (not illustrated) included in the control section 154.

The dimming control section 160 fulfills a role of executing the processes related to the dimming control method according to the present embodiment. The dimming control section 160 controls dimming in relation to the imaging of the observation target by the imaging device, according to a set dimming mode.

A dimming mode according to the present embodiment is a method of dimming control that prescribes a way to control the dimming. Multiple dimming modes with different ways of controlling dimming are included among the dimming modes according to the present embodiment.

Controlling the dimming according to the present embodiment may be, for example, any or all of controlling the exposure time of the imaging device, controlling the gain of the image signal expressing the medical captured image captured by the imaging device, and controlling the light source that irradiates the observation target with illuminating light. The imaging device related to controlling the dimming may be the imaging device included in the imaging section 150. Also, the controlling of the light source related to controlling the dimming may be, for example, controlling the light emission of the light source (not illustrated) provided inside the barrel member 122 (in the case of the medical observation apparatus 100 illustrated in FIG. 1), or controlling the light emission of the light source unit 136 (in the case of the medical observation apparatus 100 illustrated in FIG. 4).

Note that the controlling of the dimming according to the present embodiment is not limited to the examples illustrated above. For example, the controlling of the dimming according to the present embodiment may also include any control capable of altering the brightness of the observation target in the imaging by the imaging device or the brightness of the medical captured image captured by the imaging device.

One example of the dimming modes according to the present embodiment and one example of the processes related to the dimming control method according to the present embodiment will be described later.

For example, by including the dimming control section 160, the control section 154 fulfills a role of leading the execution of the processes related to the dimming control method according to the present embodiment. Also, for example, by including the imaging control section 156 and the display control section 158, the control section 154 fulfills a role of controlling the medical observation apparatus 100 overall.

Note that the functional configuration of the control section 154 is not limited to the example illustrated in FIG. 5.

For example, it is possible for the control section 154 to have any configuration corresponding to how the functions included in the medical observation apparatus 100 are divided up, such as a configuration corresponding to how the processes related to the dimming control method according to the present embodiment are divided up.

To give one example, in the case in which the medical observation apparatus 100 has the configuration illustrated in FIG. 1, the control section 154 additionally may include an arm control section (not illustrated) that controls the driving of the arm 104. One example of control of the driving of the arm 104 includes, for example, "applying a control signal that controls driving to the actuators (not illustrated) corresponding to each of the joint sections 110a, 110b, 110c, 110d, 110e, and 110f", and the like.

The medical observation apparatus 100 performs processes related to the dimming control method according to the present embodiment described later with the functional configuration illustrated in FIG. 5, for example.

Note that the functional configuration of the medical observation apparatus according to the present embodiment is not limited to the configuration illustrated in FIG. 5.

For example, in the medical observation apparatus according to the present embodiment, one or both of the imaging control section 156 and the display control section 158 illustrated in FIG. 5 can be provided separately from the control section 154 (for example, realized by a different processing circuit).

Additionally, in the medical observation apparatus according to the present embodiment, the functional configuration capable of executing the processes related to the dimming control method according to the present embodiment is not limited to the configuration illustrated in FIG. 5, and it is possible for the medical observation apparatus according to the present embodiment to take a functional configuration corresponding to how the processes related to the dimming control method according to the present embodiment are divided up.

Also, in the case in which the medical observation apparatus according to the present embodiment has the configuration illustrated in FIG. 1, the medical observation apparatus according to the present embodiment includes an arm section (not illustrated) including the arm 104. The arm 104 included in the arm section (not illustrated) supports the imaging device 106 included in the imaging section 150.

Also, for example, in the case of communicating with an external apparatus via an external communication device having a function and configuration similar to the communication section 152, the medical observation apparatus according to the present embodiment may also not be provided with the communication section 152.

Also, in the case in which the medical observation system according to the present embodiment includes a medical control apparatus (not illustrated), and the medical observation apparatus according to the present embodiment is controlled by the medical control apparatus (not illustrated), the medical observation apparatus according to the present embodiment may also not be provided with the control section 154.

Herein, the medical control apparatus (not illustrated) is, for example, provided with a control section having a function and configuration similar to the control section 154, and thereby executes processes related to the dimming control method according to the present embodiment described later, and in addition, controls the operation in each structural element such as the imaging section 150 provided in the medical observation apparatus according to the present embodiment. The medical control apparatus (not illustrated) communicates with the medical observation apparatus according to the present embodiment via a provided communication device or a connected external communication device, and thereby controls the operation in each structural element provided in the medical observation apparatus according to the present embodiment.

Furthermore, in the case in which the medical observation system according to the present embodiment includes the medical control apparatus (not illustrated), and the medical observation apparatus according to the present embodiment is controlled by the medical control apparatus (not illustrated), it is also possible for the medical observation apparatus according to the present embodiment to take a configuration that does not include some of the functions of the control section 154.

[2] Dimming Control Method According to Present Embodiment

Next, the dimming control method according to the present embodiment will be described. The following gives an example of a case in which the processes related to the dimming control method according to the present embodiment are executed by the medical observation apparatus 100 (more specifically, the dimming control section 160 of the control section 154 included in the medical observation apparatus 100, for example). Note that, as described above, in the medical observation system according to the present embodiment, the processes related to the dimming control method according to the present embodiment may also be executed by the display apparatus 200, a medical control apparatus (not illustrated), or the like.

In the case of performing surgery using the medical observation system including an electronic imaging medical observation apparatus like the medical observation apparatus 100, as illustrated by the use case illustrated with reference to FIG. 2, a surgical site of a patient acting as the observation target is imaged by the imaging device. Herein, for example, in the case in which a "medical instrument such as forceps" or a "whitish object such as gloves worn on the hands of the surgeon or an assistant, gauze, or the like" enters the capture range of the imaging device, the specular reflection of illuminating light by the medical instrument or the whitish object often causes the medical instrument or the whitish object to be imaged brighter than the surgical site originally treated as the observation target. When a medical instrument or a whitish object is imaged brighter than the surgical site as above, in the case in which typical dimming control is executed, dimming control to lower the brightness is executed, and as a result, the surgical site originally treated as the observation target is imaged darkly. Major factors that cause the surgical site originally treated as the observation target to be imaged darkly in typical dimming control are as follows, for example.

Dimming control is made to run continually on a fixed criterion, and if the brightness environment on the subject side changes, the dimming control also attempts to track the change.

Since there is an infinite variety of surgical site environments, it is difficult to set a fixed, all-purpose criterion for dimming control that works to stabilize the brightness of the surgical site in all situations.

At this point, as a method of avoiding a situation in which the surgical site originally treated as the observation target is imaged darkly as above, a method of setting a narrow photometry area or a method of setting a dull response in the dimming sensitivity. However, even if the photometry area is narrowed, in the case in which a target object enters the area, the dimming will react, and therefore this method is insufficient as a countermeasure. Also, if the response of the dimming sensitivity is dulled, it will typically take a long time for the dimming to correctly respond to changes in the environment inside the capture range, and an adverse effect is produced as a risk of annoying the person looking at the medical captured image being displayed on the display screen.

Accordingly, the medical observation apparatus 100 does not run the dimming control continually with the same criterion, and instead switches between dimming modes with different tracking speeds, and controls dimming according to the set dimming mode.

The tracking speed according to the present embodiment is one example of an evaluation standard for brightness trackability, which is evaluated according to "the time taken until the brightness obtained as a result of the dimming control (for example, the brightness of the observation target in the imaging by the imaging device or the brightness of the medical captured image captured by the imaging device; the same applies hereinafter) becomes the brightness of brightness environment on the subject side", for example. The tracking speed is changed by altering the speed of change in any or all of the exposure time of the imaging device, the image signal gain, and the illuminating light emitted by the light source, for example. The brightness of the brightness environment on the subject side is estimated by the process of estimating the brightness of the observation target on the basis of the image signal described above, or detected by a sensor (such as a luminance sensor or an illuminance sensor, for example) capable of detecting the brightness of the observation target, for example. The above sensor capable of detecting the brightness of the observation target may be a sensor provided in the medical observation apparatus 100 or a sensor external to the medical observation apparatus 100.

The dimming modes according to the present embodiment include at least the first dimming mode illustrated below and the second dimming mode illustrated below.

First dimming mode: a dimming mode that controls dimming according to a first tracking speed Second dimming mode: a dimming mode that controls dimming according to a second tracking speed that is slower than the first tracking speed To give one example, the second dimming mode is a dimming mode in which the control of dimming when a change in the brightness of the observation target (a change in the brightness environment on the subject side) occurs starts later than in the first dimming mode. For example, in the case in which the control of dimming is started in the first dimming mode when the absolute value of the difference between the brightness of the brightness environment on the subject side and a target brightness obtained by the dimming control is greater than a first threshold value, the control of dimming is started in the second dimming mode when the absolute value of the difference is greater than a second threshold value (where second threshold value>first threshold value). Each of the above first threshold value and the above second threshold value may be a preset fixed value, or a variable value that is changeable according to an operation on the medical observation apparatus 100 or the like.

Also, to give another example, the second dimming mode is a dimming mode in which the change in the brightness of the observation target per unit time is smaller than in the first dimming mode. Herein, the above unit time may be any time interval, such as 10 [s], 30 [s], or 1 [min]. Here, the second dimming mode may also include a dimming mode that does not change the brightness of the observation target.

Furthermore, the second dimming mode may also be a "dimming mode in which the control of dimming when a change in the brightness of the observation target occurs starts later than in the first dimming mode, and also in which the change in the brightness of the observation target per unit time is smaller than in the first dimming mode".

Note that the examples of dimming modes according to the present embodiment are not limited to the examples illustrated above. For example, in the case in which the second dimming mode does not include a dimming mode that does not change the brightness of the observation target, the dimming modes according to the present embodiment may also include a fixed dimming mode that does not change the brightness of the observation target.

The following gives an example of a case in which the medical observation apparatus 100 sets the first dimming mode or the second dimming mode as the dimming modes according to the present embodiment, and executes dimming control according to the set dimming mode. In other words, the following gives an example of a case in which a dimming mode that does not change the brightness of the observation target may be included in the second dimming mode.

Specifically, the medical observation apparatus 100 executes dimming control according to the first dimming mode or the second dimming mode by executing the processes in (1) and the processes in (2) below, for example.

(1) First Example of Processes Related to Dimming Control Method: Dimming Control According to First Dimming Method The medical observation apparatus 100 sets the first dimming mode on the basis of a change in imaging-related behavior in the imaging device. The medical observation apparatus 100 sets the first dimming mode when a change in imaging-related behavior in the imaging device is detected. Subsequently, the medical observation apparatus 100 executes control according to the set first dimming mode. In the following, imaging-related behavior in the imaging device will be simply designated "imaging-related behavior".

As an example of the medical observation apparatus 100 detecting a change in the imaging-related behavior, the example illustrated below may be given, for instance. Note that the example of the medical observation apparatus 100 detecting a change in the imaging-related behavior obviously is not limited to the example illustrated below.

When the medical observation apparatus 100 is powered on (example of a case in which a change in imaging-related behavior is detected in association with the startup of the medical observation apparatus 100)

When a predetermined operation on an operating device provided in the medical observation apparatus 100 or an operating device external to the medical observation apparatus 100, such as the footswitch FS, is detected (for example, when an "operation of moving the field of view, an operation of changing the focus, or an operation of changing the observation field of view such as an operation of changing the zoom", or an "operation of changing the imaging parameters, such as an operation of changing the brightness level, an operation of turning illumination on/off, an operation of changing the color mode, or an operation of executing special imaging" is detected)

The medical observation apparatus 100 sets the first dimming mode when a change in imaging-related behavior in the imaging device is detected, and starts control according to the first dimming mode. Also, the medical observation apparatus 100 executes the control according to the first dimming mode until determining that a predetermined condition described later is satisfied. Herein, it is possible to treat the period from detecting a change in imaging-related behavior in the imaging device to determining that the predetermined condition described later is satisfied as being a "period in which the medical observation apparatus 100 is in a state of transition of imaging-related behavior in the imaging device", for example. The state of transition of imaging-related behavior in the imaging device includes a "state in which imaging-related behavior in the imaging device is ongoing" and a "state in the period after imaging-related behavior in the imaging device has completed until it is determined that the predetermination condition described later is satisfied".

(2) Second Example of Processes Related to Dimming Control Method: Dimming Control According to Second Dimming Method The medical observation apparatus 100 sets the second dimming mode in the case of determining that the predetermined condition is satisfied when executing control according to the first dimming mode by the processes related to the first example illustrated in (1) above, for example. Subsequently, the medical observation apparatus 100 executes control according to the set second dimming mode.

For example, the medical observation apparatus 100 determines that the predetermined condition is satisfied when the dimming by the control according to the first dimming mode ends.

The time when the dimming by the control according to the first dimming mode ends may refer to "when the brightness obtained as a result of the dimming control matches the brightness of the brightness environment on the subject side" or "when the absolute value of the difference between the brightness obtained as a result of the dimming control and the brightness of the brightness environment on the subject side is equal to or less than a set threshold value (or when the absolute value is less than the threshold value)", for example. The above threshold value may be a preset fixed value, or a variable value that is changeable according to an operation on the medical observation apparatus 100 or the like. Note that the method of determining whether the dimming by the control according to the first dimming mode has ended obviously is not limited to the example illustrated above.

Additionally, the medical observation apparatus 100 may also determine that the predetermined condition is satisfied when a predetermined time elapses from the start of the control according to the first dimming mode. The predetermined time may be a preset fixed time interval, or a variable time interval that is changeable according to an operation on the medical observation apparatus 100 or the like.

Furthermore, the medical observation apparatus 100 may determine that the predetermined condition is satisfied in the case of fulfilling either of when the dimming by the control according to the first dimming mode ends and when a predetermined time elapses from the start of the control according to the first dimming mode.

Note that the processes related to the dimming control method according to the second example are not limited to the example illustrated above.

For example, it is also possible for the medical observation apparatus 100 to set the second dimming mode in the case in which the control according to the first dimming mode is not being executed, and execute control according to the second dimming mode.

The medical observation apparatus 100 sets the second dimming mode on the basis of a change in imaging-related behavior in the imaging device, for example. Specifically, the medical observation apparatus 100 sets the second dimming mode in the case in which a change in imaging-related behavior is not detected, for example. Subsequently, the medical observation apparatus 100 executes control according to the set second dimming mode.

For example, by executing the processes according to the first example illustrated in (1) above and the processes related to the second example illustrated in (2) above, the medical observation apparatus 100 is able to execute dimming control by switching between the first dimming mode and the second dimming mode with different tracking speeds.

FIG. 6 is a flowchart illustrating one example of the processes related to the dimming control method according to the present embodiment, and illustrates one example of the processes in the case in which the medical observation apparatus 100 executes dimming control by switching between the first dimming mode and the second dimming mode.

The medical observation apparatus 100 determines whether or not the system is running (S100). The medical observation apparatus 100 determines that the system is running in the case in which a change in imaging-related behavior is detected, for example. The state in which the system is determined to be running corresponds to the state in which imaging-related behavior in the imaging device is ongoing.

In the case of determining that the system is running in step S100, the medical observation apparatus 100 sets the first dimming mode and executes dimming control according to the first dimming mode (S102). By executing dimming control according to the first dimming mode, even if there is a change in the environment inside the capture range, the brightness obtained as a result of the dimming control can be suited to the brightness of the brightness environment on the subject side more rapidly than in the case of executing dimming control according to the second dimming mode.

When the process in step S102 is executed, the medical observation apparatus 100 determines whether or not the system has finished running (S104). For example, the medical observation apparatus 100 determines that the system has finished running when the startup of the medical observation apparatus 100 is completed or when a process corresponding to a predetermined operation on an operating device or the like provided in the medical observation apparatus 100 is completed.

In the case of not determining that the system has finished running in step S104, the medical observation apparatus 100 repeats the processes from step S102.

Also, in the case of determining that the system has finished running in step S104, the medical observation apparatus 100 executes dimming control according to the first dimming mode (S106). At this point, the medical observation apparatus 100 may set the dimming mode back to the first dimming mode again, or take up the setting of the first dimming mode set in step S102. The dimming control according to the first dimming mode in step S106 corresponds to dimming control in a state of transition of imaging-related behavior in the imaging device.

When the process in step S106 is executed, the medical observation apparatus 100 determines whether or not the predetermined condition is satisfied (S108).

In the case in which the predetermined condition is not determined to be satisfied in step S108, the medical observation apparatus 100 repeats the processes from step S106. Also, in the case in which the predetermined condition is determined to be satisfied in step S108, the medical observation apparatus 100 repeats the processes from step S100.

In the case of not determining that the system is running in step S100, the medical observation apparatus 100 sets the second dimming mode and executes dimming control according to the second dimming mode (S110). By executing dimming control according to the second dimming mode, the tracking speed in the case of a change in the environment inside the capture range becomes slower than in the case of executing dimming control according to the first dimming mode.

At this point, the case of not determining that the system is running refers to the case in which a change in imaging-related behavior is not detected. For this reason, in the case of not determining that the system is running, change in the environment of the observation target inside the capture range is considered to be small. For this reason, in the case of not determining that the system is running, there is considered to be little need to rapidly match the brightness obtained as a result of the dimming control to the brightness of the brightness environment on the subject side.

Also, by executing dimming control according to the second dimming mode in step S110, even in the case in which specular reflection from a medical instrument or a whitish object enters the capture range, an overreaction in dimming caused by these factors is avoided.

The medical observation apparatus 100 executes the processes illustrated in FIG. 6 for example as the processes related to the dimming control method according to the present embodiment. At this point, the medical observation apparatus 100 does not run the dimming control continually with the same criterion, and instead switches between the first dimming mode and the second dimming mode having different tracking speeds to execute dimming control.

Therefore, by executing the processes illustrated in FIG. 6, the medical observation apparatus 100 is able to execute dimming control better suited to the imaging of the observation target by the imaging device. Note that the example of the processes related to the dimming control method according to the present embodiment obviously is not limited to the example illustrated in FIG. 6.

Note that the processes related to the dimming control method according to the present embodiment are not limited to the example illustrated above.

For example, the medical observation apparatus 100 may activate a function of setting the second dimming mode or deactivate the function of setting the second dimming mode on the basis of a predetermined operation. In other words, it is also possible for the medical observation apparatus 100 to selectively activate a function of switching from dimming control according to the first dimming mode to dimming control according to the second dimming mode. In the case in which the function of setting the second dimming mode is deactivated, the medical observation apparatus 100 executes dimming control according to the first dimming mode, for example.

The predetermined operation according to the present embodiment may be, for example, an operation of switching the above function performed on an operating device provided in the medical observation apparatus 100, an operation of switching the above function performed on an external operating device such as a remote controller or the foot-switch FS, or the like.

Also, the medical observation apparatus 100 additionally may execute a process of issuing a notification about the set dimming mode, for example.

For example, the medical observation apparatus 100 issues a visual notification about the set dimming mode by causing one or both of text indicating the set dimming mode and an image such as an icon indicating the set dimming mode to be display on any display screen visible to the user of the medical observation apparatus 100, such as the display screen of the display apparatus 200. Also, for example, the medical observation apparatus 100 issues an aural notification about the set dimming mode by causing sound indicating the set dimming mode to be output from a sound output device such as a speaker. Furthermore, the medical observation apparatus 100 may also issue a notification about the set dimming mode by both a visual notification method and an aural notification method. The above sound output device may be a sound output device provided in the medical observation apparatus 100 or a sound output device external to the medical observation apparatus 100.

By being notified of the set dimming mode, the user of the medical observation apparatus 100 is able to recognize what kind of dimming mode is being used by the medical observation apparatus 100 to execute dimming control.

Note that the process of issuing a notification about the set dimming mode is not limited to the example illustrated above. For example, the medical observation apparatus 100 may also issue a notification about whether a function of setting the second dimming mode is activated or deactivated by one or both of a visual notification method and an aural notification method.

[3] Example of Advantageous Effects Exhibited by Use of Dimming Control Method According to Present Embodiment By using the dimming control method according to the present embodiment, the advantageous effects illustrated below are exhibited, for example. Note that the advantageous effects exhibited by using the dimming control method according to the present embodiment obviously are not limited to the examples illustrated below.

By executing dimming control rapidly when the running state of the system is a state of varying brightness of the observation target, a medical captured image with more suitable brightness can be obtained rapidly.

By dulling or locking the dimming in a state in which the brightness of the observation target varies little, unintentional brightness variations are no longer tracked, and a medical captured image in a state with the dimming matched to the target that the user of the medical observation apparatus 100 truly wants to observe can be provided to the user of the medical observation apparatus 100.

(Program According to Present Embodiment)

By having a program (for example, a program capable of executing the processes related to the dimming control method according to the present embodiment) for causing a computer system to function as the medical observation apparatus according to the present embodiment (or the medical dimming control apparatus according to the present embodiment) be executed by a processor or the like in the computer system, dimming control better suited to the imaging of the observation target by the imaging device can be executed. Herein, the computer system according to the present embodiment may be a single computer or multiple computers. A series of processes related to the dimming control method according to the present embodiment is executed by the computer system according to the present embodiment.

Additionally, by having the program for causing a computer system to function as the medical observation apparatus according to the present embodiment (or the medical dimming control apparatus according to the present embodiment) be executed by a processor or the like in the computer system, the advantageous effects exhibited by the display realized by the processes related to the dimming control method according to the present embodiment described above can be exhibited.

It should be understood by those skilled in the art that various modifications, combinations, sub-combinations and alterations may occur depending on design requirements and other factors insofar as they are within the scope of the appended claims or the equivalents thereof.

For example, although the above illustrates the provision of a program (computer program) for causing a computer system to function as the medical observation apparatus according to the present embodiment (or the medical dimming control apparatus according to the present embodiment), in the present embodiment, the above program may also be provided in conjunction with a recording medium on which the above program is stored.

The configuration described above illustrates one example of the present embodiment, and rightfully belongs to the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification. Additionally, the present technology may also be configured as below.

(1) A medical dimming control apparatus including:
   a dimming control section configured to control a dimming in relation to an imaging of an observation target by an imaging device in accordance with a set dimming mode, in which
   the dimming mode at least includes a first dimming mode that controls the dimming at a first tracking speed and a second dimming mode that controls the dimming at a second tracking speed that is slower than the first tracking speed, and
   the dimming control section
   sets the first dimming mode on the basis of a change in an imaging-related behavior in the imaging device, and
   sets the second dimming mode in a case of determining that a predetermined condition is satisfied while executing the control in accordance with the first dimming mode.

(2) The medical dimming control apparatus according to (1), in which
   the dimming control section executes any or all of controlling an exposure time of the imaging device, controlling a gain of an image signal expressing a medical captured image captured by the imaging device, and controlling a light source that irradiates the observation target with illuminating light as the control of the dimming.

(3) The medical dimming control apparatus according to (1) or (2), in which
   the dimming control section determines that the predetermined condition is satisfied when the dimming by the control according to the first dimming mode ends.

(4) The medical dimming control apparatus according to any one of (1) to (3), in which
   the dimming control section determines that the predetermined condition is satisfied when a predetermined time elapses from a start of the control according to the first dimming mode.

(5) The medical dimming control apparatus according to any one of (1) to (4), in which
   the second dimming mode is a dimming mode in which the control of the dimming when a change in a brightness of the observation target occurs starts later than in the first dimming mode.

(6) The medical dimming control apparatus according to any one of (1) to (5), in which
the second dimming mode is a dimming mode in which a change in a brightness of the observation target per a unit time is smaller than in the first dimming mode.
(7) The medical dimming control apparatus according to (6), in which
the second dimming mode is a dimming mode that does not change the brightness of the observation target.
(8) The medical dimming control apparatus according to any one of (1) to (7), in which
the dimming control section
starts the control according to the first dimming mode when a change in the imaging-related behavior in the imaging device is detected, and
executes the control according to the first dimming mode until the predetermined condition is determined to be satisfied.
(9) The medical dimming control apparatus according to any one of (1) to (8), in which
the dimming control section activates or deactivates a function of setting the second dimming mode on the basis of a predetermined operation.
(10) The medical dimming control apparatus according to any one of (1) to (9), in which
the dimming control section causes a notification about the set dimming mode to be issued.
(11) The medical dimming control apparatus according to any one of (1) to (10), further including:
an arm including multiple links joined to each other by one or multiple joint sections; and
the imaging device supported by the arm.
(12) The medical dimming control apparatus according to any one of (1) to (10), further including:
the imaging device that is inserted into an inside of a body of a patient and images the inside of the body as the observation target.
(13) A dimming control method executed by a medical dimming control apparatus, the dimming control method including:
controlling a dimming in relation to an imaging of an observation target by an imaging device in accordance with a set dimming mode, in which
the dimming mode at least includes a first dimming mode that controls the dimming at a first tracking speed and a second dimming mode that controls the dimming at a second tracking speed that is slower than the first tracking speed, and
the controlling
sets the first dimming mode on the basis of a change in an imaging-related behavior in the imaging device, and
sets the second dimming mode in a case in which a predetermined condition is determined to be satisfied while executing the control in accordance with the first dimming mode.

What is claimed is:

1. A medical dimming control apparatus comprising:
processing circuitry configured to control a dimming in relation to an imaging of an observation target by an imaging device in accordance with a set dimming mode, wherein
the dimming mode at least includes a first dimming mode that controls the dimming at a first tracking speed and a second dimming mode that controls the dimming at a second tracking speed that is slower than the first tracking speed,
the processing circuitry is configured to set the first dimming mode in response to detecting a change in an imaging-related behavior in the imaging device, and set the second dimming mode in a case of determining that a predetermined condition is satisfied while executing the control in accordance with the first dimming mode,
the processing circuitry is configured to determine that the predetermined condition is satisfied and reduce a tracking speed for the dimming from the first tracking speed of the first dimming mode down to the second tracking speed of the second dimming mode in response to determining either (1) a brightness obtained as a result of setting the first dimming mode matches a brightness of a brightness environment of the observation target, or (2) an absolute value of a difference between the brightness obtained as the result of setting the first dimming mode and the brightness of the brightness environment of the observation target is equal to or less than a threshold value,
the tracking speed indicates brightness trackability, which is evaluated according to time taken until a brightness obtained as a result of controlling the dimming becomes the brightness of the brightness environment of the observation target, and
the reduction of the tracking speed is performed by reducing a speed of change in any or all of an exposure time of the imaging device, an image signal pain of an image signal expressing a medical captured image captured by the imaging device, and illuminating light emitted by a light source that irradiates the observation target.

2. The medical dimming control apparatus according to claim 1, wherein
the second dimming mode is a dimming mode in which the control of the dimming when a change in a brightness of the observation target occurs starts later than in the first dimming mode.

3. The medical dimming control apparatus according to claim 1, wherein
the second dimming mode is a dimming mode in which a change in a brightness of the observation target per a unit time is smaller than in the first dimming mode.

4. The medical dimming control apparatus according to claim 3, wherein
the second dimming mode is a dimming mode that does not change the brightness of the observation target.

5. The medical dimming control apparatus according to claim 1, wherein
the processing circuitry is configured to:
start the control according to the first dimming mode when a change in the imaging-related behavior in the imaging device is detected, and
execute the control according to the first dimming mode until the predetermined condition is determined to be satisfied.

6. The medical dimming control apparatus according to claim 1, wherein
the processing circuitry is further configured to activate or deactivate a function of setting the second dimming mode on a basis of a predetermined operation.

7. The medical dimming control apparatus according to claim 1, wherein
the processing circuitry is configured to cause a notification about the set dimming mode to be issued.

8. The medical dimming control apparatus according to claim 1, further comprising:
an arm including multiple links joined to each other by one or multiple joint sections; and
the imaging device supported by the arm.

9. The medical dimming control apparatus according to claim 1, further comprising:
the imaging device that is inserted into an inside of a body of a patient and images the inside of the body as the observation target.

10. The medical dimming control apparatus according to claim 1, wherein
the processing circuitry is configured to automatically set the second dimming mode without requiring any operation in a case of determining that the dimming by the control according to the first dimming mode ends.

11. A dimming control method executed by a medical dimming control apparatus, the dimming control method comprising:
controlling, using processing circuitry, a dimming in relation to an imaging of an observation target by an imaging device in accordance with a set dimming mode, wherein
the dimming mode at least includes a first dimming mode that controls the dimming at a first tracking speed and a second dimming mode that controls the dimming at a second tracking speed that is slower than the first tracking speed,
the controlling
sets the first dimming mode in response to detecting a change in an imaging-related behavior in the imaging device, and
sets the second dimming mode in a case in which a predetermined condition is determined to be satisfied while executing the control in accordance with the first dimming mode,
the method further comprises determining, using the processing circuitry, that the predetermined condition is satisfied and reducing a tracking speed for the dimming from the first tracking speed of the first dimming mode down to the second tracking speed of the second dimming mode in response to determining either (1) a brightness obtained as a result of setting the first dimming mode matches a brightness of a brightness environment of the observation target, or (2) an absolute value of a difference between the brightness obtained as the result of setting the first dimming mode and the brightness of the brightness environment of the observation target is equal to or less than a threshold value,
the tracking speed indicates brightness trackability, which is evaluated according to time taken until a brightness obtained as a result of controlling the dimming becomes the brightness of the brightness environment of the observation target, and
the reducing of the tracking speed is performed by reducing a speed of change in any or all of an exposure time of the imaging device, an image signal gain of an image signal expressing a medical captured image captured by the imaging device, and illuminating light emitted by a light source that irradiates the observation target.

12. A medical imaging system comprising:
an imaging device configured to image an observation target;
a display configured to display an image of the observation target captured by the imaging device; and
processing circuitry configured to control a dimming in relation to an imaging of the observation target by the imaging device in accordance with a set dimming mode, wherein
the dimming mode at least includes a first dimming mode that controls the dimming at a first tracking speed and a second dimming mode that controls the dimming at a second tracking speed that is slower than the first tracking speed,
the processing circuitry configured to set the first dimming mode in response to detecting a change in an imaging-related behavior in the imaging device, and set the second dimming mode in a case of determining that a predetermined condition is satisfied while executing the control in accordance with the first dimming mode,
the processing circuitry is configured to determine that the predetermined condition is satisfied and reduce a tracking speed for the dimming from the first tracking speed of the first dimming mode dozen to the second tracking speed of the second dimming mode in response to determining either (1) a brightness obtained as a result of setting the first dimming mode matches a brightness of a brightness environment of the observation target, or (2) an absolute value of a difference between the brightness obtained as the result of setting the first dimming mode and the brightness of the brightness environment of the observation target is equal to or less than a threshold value,
the tracking speed indicates brightness trackability, which is evaluated according to time taken until a brightness obtained as a result of controlling the dimming becomes the brightness of the brightness environment of the observation target, and
the reduction of the tracking speed is performed by reducing a speed of change in any or all of an exposure time of the imaging device image signal gain of an image signal expressing a medical captured image captured by the imaging device, and illuminating light emitted by a light source that irradiates the observation target.

* * * * *